United States Patent [19]

Fujii et al.

[11] Patent Number: 4,597,292
[45] Date of Patent: Jul. 1, 1986

[54] ULTRASONIC MEASUREMENT METHOD AND APPARATUS THEREFOR

[75] Inventors: Tadashi Fujii, Fuji; Yoshinori Hayakawa, Sakura, both of Japan

[73] Assignee: Terumo Corporation, Tokyo, Japan; by said Tadashi Fujii

[21] Appl. No.: 725,797

[22] Filed: Apr. 22, 1985

[30] Foreign Application Priority Data

Jun. 28, 1984 [JP] Japan ................. 59-131918

[51] Int. Cl.$^4$ ............................................. G01N 29/04
[52] U.S. Cl. ......................................... 73/599; 73/626
[58] Field of Search ................ 73/599, 626, 628, 641; 128/660

[56] References Cited

U.S. PATENT DOCUMENTS

4,545,250 10/1985 Miwa ..................................... 73/599
4,546,772 10/1985 Flax ....................................... 73/599

FOREIGN PATENT DOCUMENTS

91768 10/1983 European Pat. Off. .
143476 11/1980 Japan .
147082 11/1981 Japan .
82/02781 8/1982 PCT Int'l Appl. .

OTHER PUBLICATIONS

Radar Handbook by Merrill I. Skolnik.
Ultrasonic Material Testing, Revised Edition; Edited by Japan Society for the Promotion of Science.
Ultrasonic Synthetic Aperture Imaging with Nonlinear Processing Flat Detection by Synthetic Aperture Ultrasonic Imaging Method.
Journal of the Acoustical Society of America, vol. 69, No. 6, Jun. 1981, pp. 1838-1840, Acoust. Soc. Am., N.Y., US; Y. Hayakawa et al: Multifrequency Echoscopy for Quantitative Acoustical Characterization of Living Tissues.
T. Sato et al: Super-Resolution Ultrasonic Imaging by Combined Spectral and Aperture Synthesis, vol. 64, No. 2, Aug. 1977, pp. 341-345.
1972 IEEE Ultrasonics Symposium Proceedings, 72 CHO 708-8 SU, pp. 81-86, N.Y., US: E. P. Papadakis et al: New Uses of Ultrasonic Spectrum Analysis.

*Primary Examiner*—Anthony V. Ciarlante
*Attorney, Agent, or Firm*—Frishauf, Holtz, Goodman & Woodward

[57] ABSTRACT

An ultrasonic transducer is adapted to transmit spherical ultrasonic waves which have a plurality of frequencies into an object under examination while being scanned in a direction at right angles to the direction of transmission. By repeating this operation, echo signals are obtained, on the basis of which a B-scan distribution image of the echo signals is obtained through use of a synthetic aperture method. Using the distribution image, there is determined position information relating to positions of interest in the object as indicated in the distribution image, as well as scanning positions of the ultrasonic transducer situated on extensions of straight lines connecting the positions of interest. The attenuation coefficient of the object is measured based on echo signals at the scanning positions.

7 Claims, 23 Drawing Figures

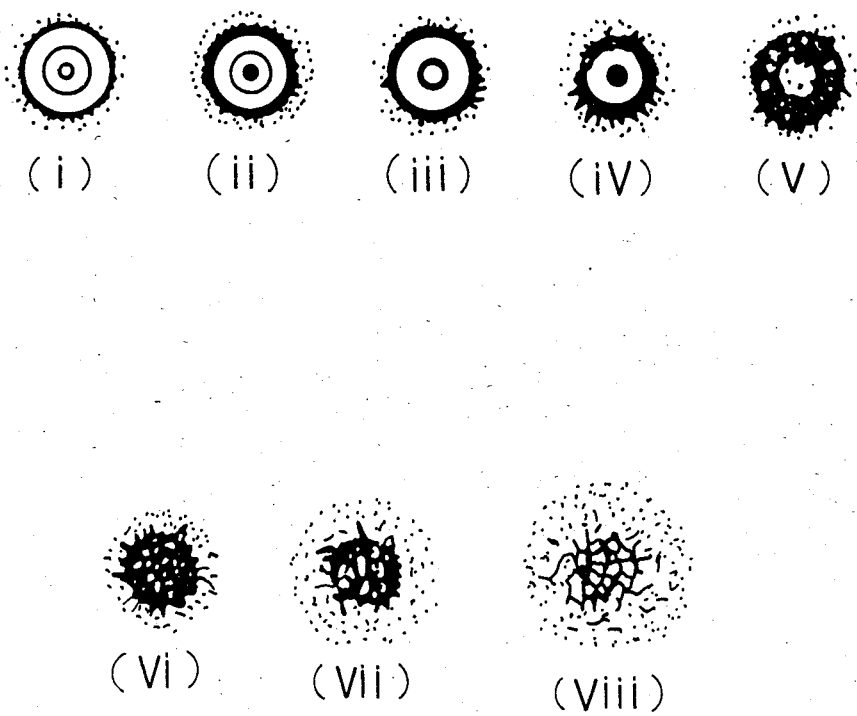

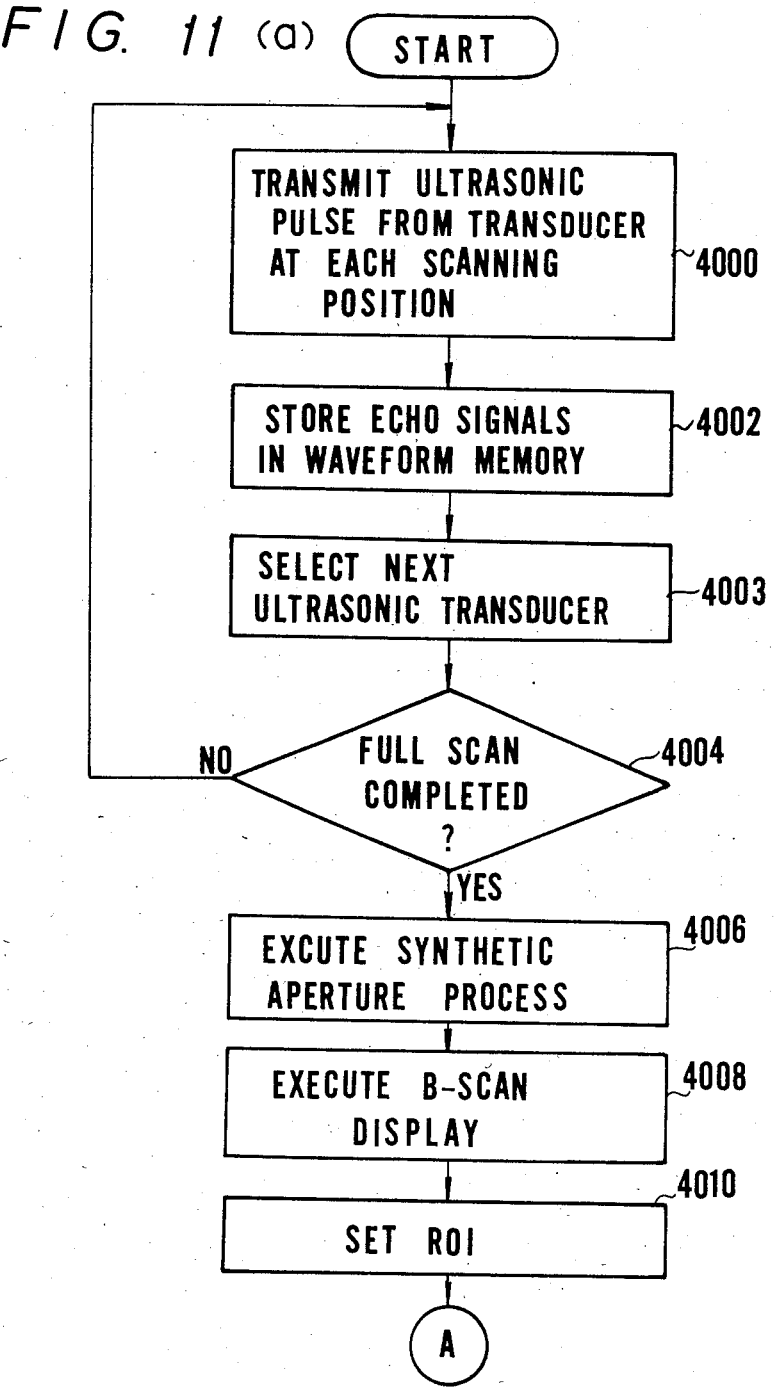

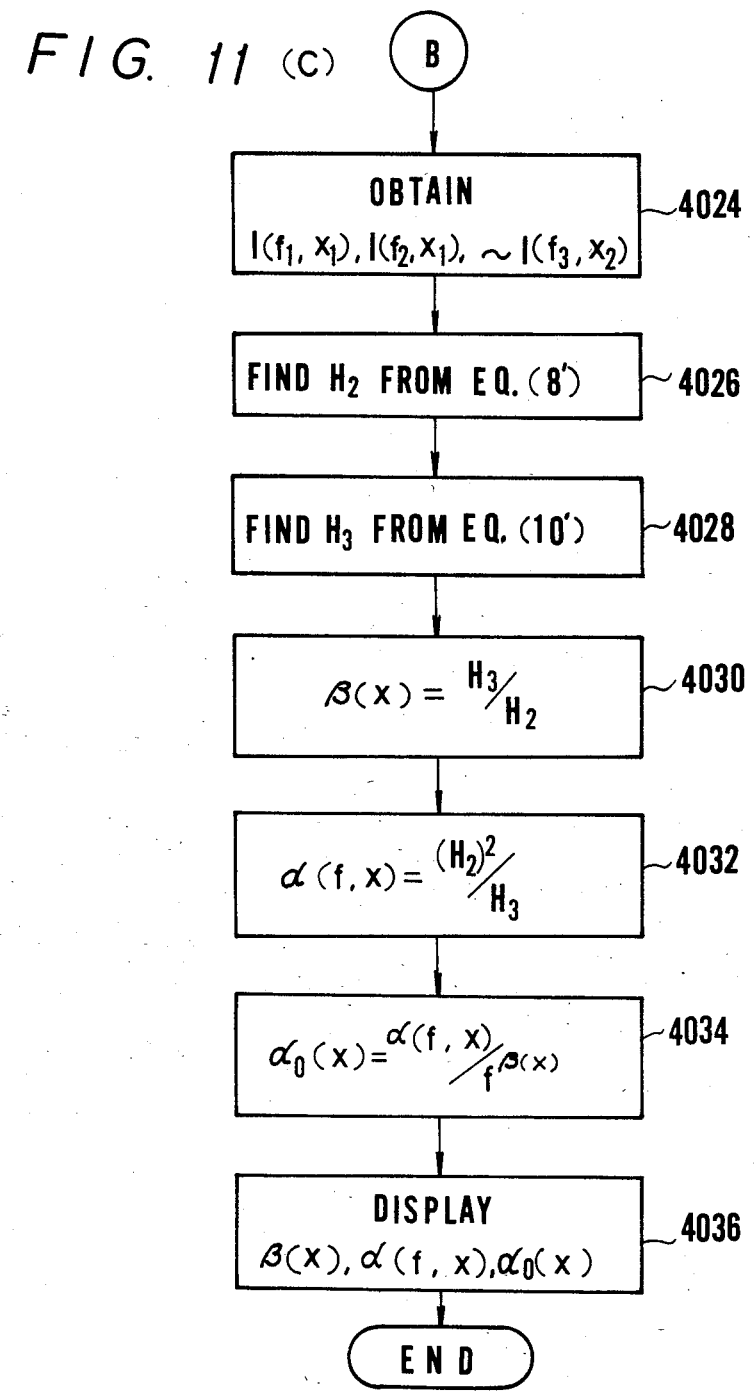

ULTRASONIC MEASUREMENT METHOD AND APPARATUS THEREFOR

BACKGROUND OF THE INVENTION

This invention relates to improvements in an ultrasonic measurement method for subjecting an object to an ultrasonic transmission and receiving reflected ultrasonic waves from the interior of the object to measure the acoustic characteristics of the interior. More particularly, the invention relates to an ultrasonic measurement method and apparatus for providing information relating to attenuation that accompanies propagation of ultrasonic waves in the interior of an object.

Ultrasonic measurement techniques find application widely in such fields as material testing, SONAR and medical diagnosis. In ultrasound material testing, measuring the degree of attenuation of ultrasonic waves in an object under examination is one of the most useful expedients for clarifying the physical and material properties of the object. In a case where the size of a flaw in a specimen exhibiting a high degree of ultrasonic attenuation is estimated when examining for flaws by using an ultrasonic flaw detector, it is necessary to apply a correction to compensate for the amount of attenuation. To accomplish this, there is a need for accurate measurement of attenuation coefficients.

A problem encountered in this regard is that sound intensity gradually decreases owing to gradual spreading of an ultrasonic wavefront caused by diffraction when the ultrasonic waves propagate internally of the object. This phenomenon, referred to as diffusion loss, must be corrected for without fail when measuring an attenuation coefficient. Correction for diffusion loss is described in detail in Chapter 6 of *Ultrasonic Material Testing* published by the Nikkan Kogyo Shimbun Ltd., in which it is stated that correction is made by performing a comparative measurement using a reference specimen for measuring attentuation. The reference specimen is required to have the same geometry, dimensions, surface conditions and acoustic impedence as the object undergoing measurement, to have a known attenuation coefficient and to be so small that attenuation is negligible. Accordingly, it does not always follow that a reference specimen in line with the object under measurement can be fabricated.

Let us now discuss the reasons why a practical correction must be made using such a reference specimen. As well known, ultrasonic waves encounter an interference or diffraction phenomenon, with the result that the transmission sound field characteristic of, e.g., a disc transducer having a finite aperture defines a complicated pattern or field, as shown in FIGS. 2(a) through 2(c). FIG. 2(a) shows that almost all the ultrasonic energy lies within the limits shown. FIG. 2(b) shows the distribution of the relative intensity Ix/Im along the central axis of the beam, where amplitude Ix represents sound intensity at a position X, and Im represents maximum sound intensity along the X axis. FIG. 2(c) shows the energy distribution of beam cross-sections at positions (i) through (viii) along the X axis in FIG. 2(b). Xmax in FIG. 2(b) denotes the last position where maximum intensity along the X axis occurs. Even for the same attenuating medium, therefore, the characteristics of the transmitted ultrasonic beam incident upon the medium differ depending upon the distance X from the transducer, as shown in FIGS. 2(a) through 2(c). Moreover, the sound fields ordinarily used for measurement are in the neighborhood of the more complex near sound fields, so applying a theoretical correction involves considerable difficulty. It is for this reason that a reference specimen is used in the prior art in order to correct for diffusion loss.

SUMMARY OF THE INVENTION

The present invention has been devised to eliminate the aforementioned drawbacks encountered in the prior art and the object thereof is to provide a method and apparatus for measuring an attenuation coefficient of an object under examination, wherein an attenuation coefficient measurement error ascribable to diffusion loss is minimized without relying upon a reference specimen for attenuation measurement.

According to the present invention, the foregoing object is attained by providing an ultrasonic measurement method, comprising successively scanning ultrasonic transceiving means, which is adapted to transmit generally spherical ultrasonic waves having at least three frequency components toward an object under examination, substantially at right angles to a direction in which the ultrasonic waves are transmitted, during which time the transceiving means receives an echo from the object, measuring the intensity of a reflected wave based on the echo and performing a calculation using a synthetic aperture method to obtain a B-scan distribution image of the intensity in the object, and obtaining an attenuation coefficient of the object based on the intensity of the reflected wave for a scanning position of the transceiving means generally on an extension of a line connecting plural positions of interest designated in the obtained B-scan distribution image.

According to a characterizing feature of the present invention, when a sound pressure of the transmitted ultrasonic waves is solely inversely proportional to the square of the propagation distance within the object under examination, attenuation coefficient can be calculated without influence of the diffusion loss which is caused by the propagation.

According to another characterizing feature of the present invention, when more than two positions of interest are at the same distance from the scanning position, another scanning position is found and an attenuation coefficient is calculated based on the intensity of the reflected wave for the other scanning position.

According to another aspect of the present invention, the foregoing object is attained by providing an ultrasonic measurement apparatus comprising transceiving means having an ultrasonic transducer for transmitting generally spherical ultrasonic waves having at least three frequency components toward an object under investigation, and for receiving an echo signal from the object, and scanning means for successively scanning the ultrasonic transducer substantially at right angles to a direction in which the ultrasonic waves are transmitted, first arithmetic means for measuring the intensity of a reflected wave based on the echo signal and for performing a calculation based on a synthetic aperture method to obtain a B-scan distribution image of the intensity in the object, designating means for designating plural positions of interest in the B-scan distribution image obtained, and second arithmetic means for obtaining an attenuation coefficient of the object based on the intensity of the reflected wave for a scanning position of the ultrasonic transducer generally on an extension of a line connecting the plural positions of interest designated.

According to another characterizing feature of the present invention, the second arithmetic means is adapted to calculate a sound pressure of the transmitted ultrasonic waves is solely inversely proportional to the square of the propagation distance within the object under examination, attenuation coefficient can be calculated without influence of the diffusion loss which is caused by the propagation.

According to another characterizing feature of the present invention, when more than two positions of interest are at the same distance from the scanning position, another scanning position is found and the apparatus can calculate an attenuation coefficient based on the intensity of the reflected wave for the other scanning position.

According to still another characterizing feature of the present invention, the designating means has display means for visually displaying the B-scan distribution image, with the positions of interest being designated based on the B-scan distribution image displayed on the display means. The second arithmetic means is further adapted to display the obtained attenuation coefficient on the display means.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

Before describing a preferred embodiment of the present invention in detail, we shall discuss the principle of ultrasonic flaw detection based on a synthetic aperture method employed in the present invention.

The sythentic aperture method is one of the image forming methods long known in the radar field as synthetic aperture radar. For a detailed discussion of the synthetic aperature method, see for example Chapter 23 of the *Radar Handbook*, edited by M. L. Skolnik and published by the McGraw-Hill Book Company. An example of this principle applied to a method of ultrasonic flaw detection is set forth in "*Flaw Detection by the Synthetic Aperture Ultrasonic Imaging Method*", Vol. 30, No. 9, p. 720 of *Non-destructive Inspections* in the summaries of convention lectures held in the fall of 1981. According to the description given, image information such as a scan or tomograph of an object under investigation is obtained by successively transmitting ultrasonic signals toward the object from a plurality of positions, receiving signals, which are reflected from within the object, at a plurality of aperture planes, and analyzing, editing and synthesizing the signals thus received, thereby obtaining the aforesaid information.

Figure 3:
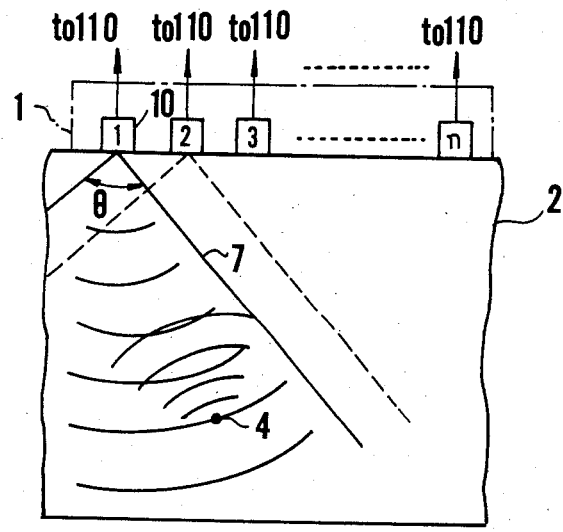
FIGS. 3(a) and (b) are explanatory views illustrating the principle of a synthetic aperture method.
Figure 3:
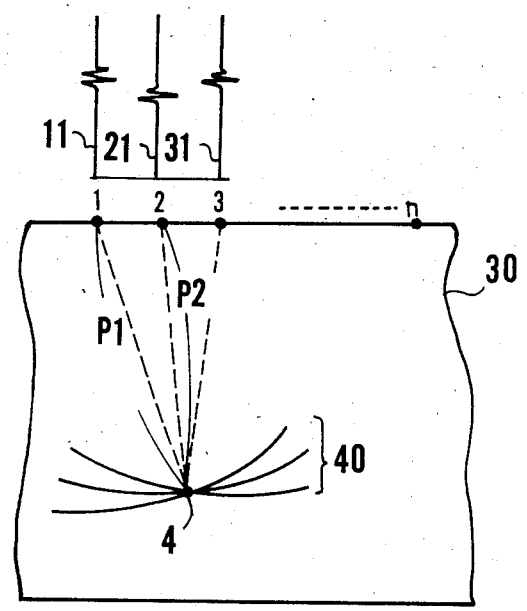
Figure 4:
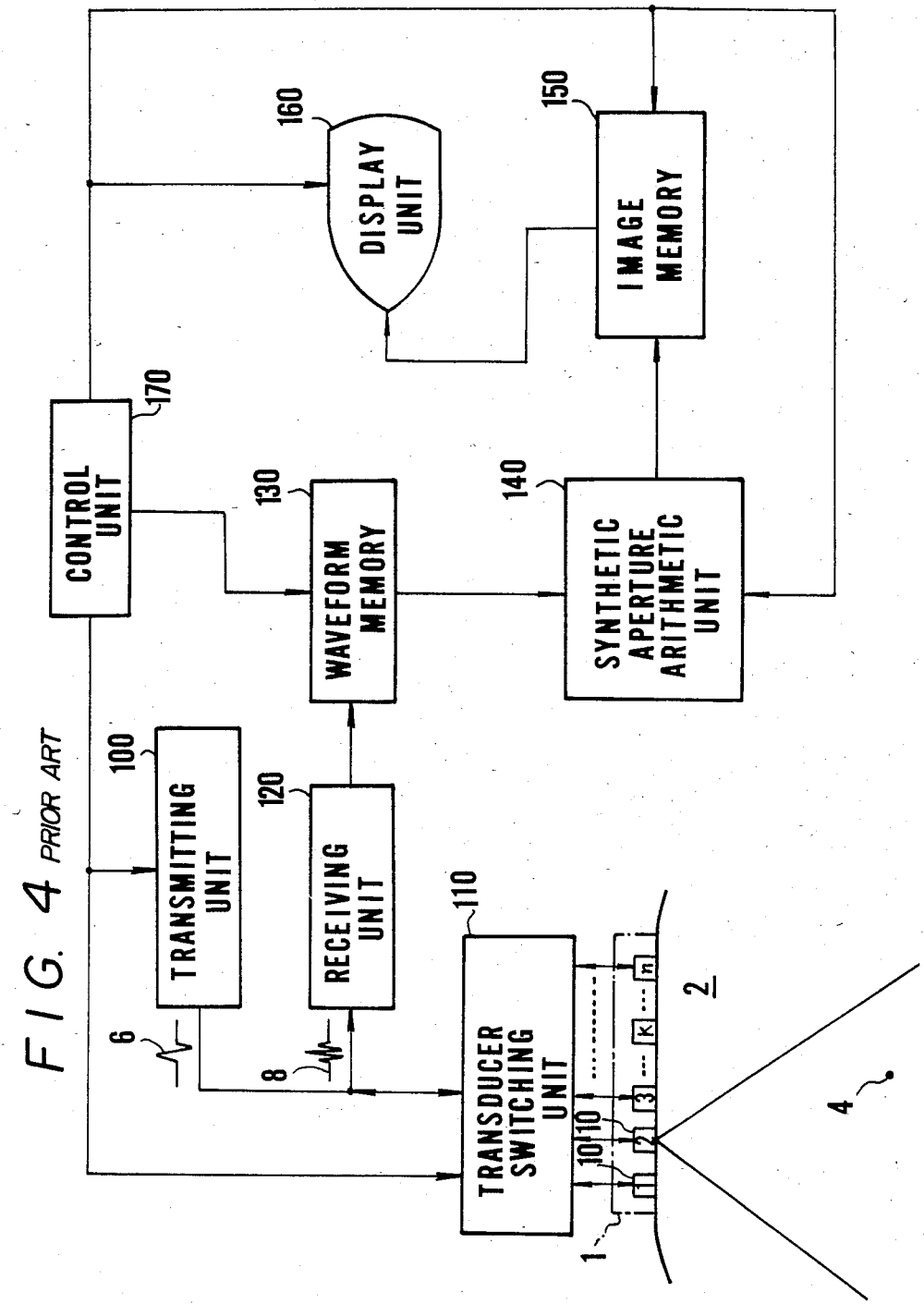
FIG. 4 is a block diagram illustrating an example of a prior-art ultrasonic measurement apparatus using the synthetic aperture method.

Let us describe this principle in simple fashion in accordance with FIGS. 3(a), (b) and 4, in which FIGS. 3(a) and (b) illustrate the aforementioned ultrasonic flaw detection method using the synthetic aperture technique, and FIG. 4 shows a conventional apparatus for practicing the method. A probe 1 comprises n-number of transducers 10 each of which has a wide angle of beam directivity. The first (leftmost) transducer responds to a drive signal 6 from a transmitting unit 100 by transmitting, into an object 2 undergoing measurement, ultrasonic waves spread over a wide angle $\theta$ of directivity, as shown for example at 7 in FIG. 3(a). An echo which results from reflection of the ultrasonic waves at a flaw 4 in the object 2 is received by the first transducer, which responds by producing a reception signal 8 (FIG. 4). The signal 8 is amplified to a required magnitude by a receiving unit 120 and then has its amplitude and phase stored in a waveform memory 130, shown in FIG. 4.

The second transducer performs an identical transmission and reception operation to produce a reception signal which is likewise stored in the waveform memory 130. The same operations are performed by each of all transducers from the third onward. Thus, the first to the n-th transducers are scanned by a transducer switching unit 110 as each executes a transceiving operation in successive fashion. As the result of a scan, the amplitudes and phases of all echo signals received by the entirety of transducers will come to be stored in the waveform memory 130. In other words, the equivalent of an ultrasonic hologram of the object 2 will be formed in the waveform memory 130.

A synthetic aperture arithmetic unit 140 performs a calculation to obtain a tomograph of the object 2 from the data stored in the waveform memory 130. To this end, various methods using synthetic aperture algorithms are available and research into improvements is presently underway. The general features of one example are disclosed in "Ultrasonic Synthetic Aperture Imaging with Nonlinear Processing", 41-PE-33, p. 587, of the collected papers presented at the lectures of the 41st Japan Society of Ultrasonics in Medicine (1982). Let us describe in brief a method of cumulative addition, which is the most basic of the algorithms.

As shown in FIGS. 3(a) and 3(b), on the basis of a received waveform 11 obtained at the first transducer, a concentric circle centered on the first transducer and the radius whereof is the echo pulse reception time period (i.e., phase P1) is described on an image reconstruction plane 30, and a value corresponding to the echo amplitude is written on the concentric circle. Likewise, for a received waveform 21 obtained at the second transducer, a value corresponding to the echo amplitude is written and superposed on a concentric circle having a phase P2 as its radius. This process is repeated for all transducers up to the n-th transducer, whereby locii of the kind shown at 40 are described on the image reconstruction plane 30. An image of the flaw 4 is formed by the concentrated intersection of the locii, which are defined by the concentric circles, at a position in the image reconstruction plane that corresponds to the position of the flaw 4.

Assuming that the propagation velocity of sound in the object 2 is either known or a certain fixed value C, we can obtain the distance from the surface of the object 2 to the flaw 4 by calculating ½Ct, where t is the time needed for an echo to be received from the flaw 4 at a point on the surface of the object directly above the flaw. An image obtained in this manner is fed into an image memory 150 and displayed as an intensity-modulated tomograph on a display unit 160, such as a CRT. The apparatus is under the overall control of a control unit 170.

The image obtained by the synthetic aperture method has a spatial resolution over the entirety of the image that is a vast improvement over that of the B-scan image based on a conventional pulse-echo technique. The reasons for this improvement are set forth in detail in the *Radar Handbook* mentioned earlier and will not be described here.

Though the image obtained in the foregoing manner does represent a great improvement over the conventional image in terms of spatial resolution, the acquired information is exactly the same as that provided by the conventional B-scan image, namely a two-dimensional distribution image at a boundary or interface where the acoustic impedance of the object 2 differs. In other words, the information obtained does not go beyond morphological information representative of the object undergoing measurement. To be more specific, it is presumed that attenuation which accompanies propagation of ultrasonic waves in an object is dealt with by a base-line correction method, which is the conventional way of correcting for attenuation, or by a so-called STC (sensitivity time control) method. This is to say, it is thought that attenuation is corrected for either by performing a cumulative addition after an STC correction has been applied to an original signal, namely a signal prior to reproduction as an image (i.e., the signals 11, 21, 31 . . . in FIG. 3(b)), or by externally applying an STC correction at one's volition in such a manner that a finally reproduced image is averaged to exhibit a substantially constant brilliance from the surface of the image down to the depths thereof.

There have been several reports describing application of the synthetic aperture method to ultrasonic flaw detection and to ultrasonic diagnostic systems for medical purposes, as mentioned above. Improved methods have also been disclosed as for example in the specification of Japanese Patent Application Laid-Open No. 55-143476. Nevertheless, all of these methods either ignore attenuation or apply a correction using an STC method of the kind set forth above.

Figure 5:
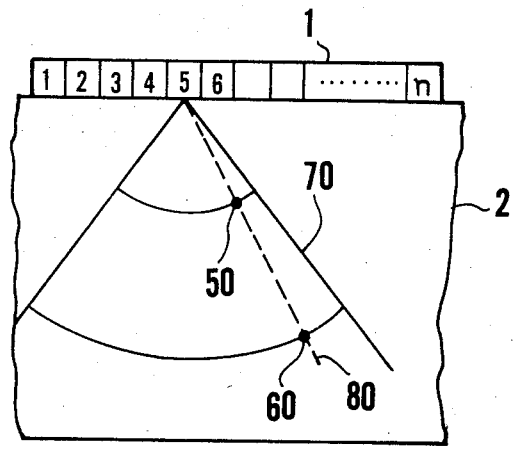
FIGS. 5(a),(b),(c)
Figure 5:
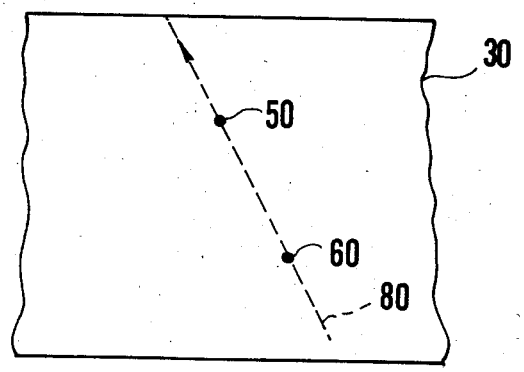
Figure 5:
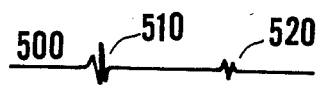

According to the present invention, the attenuation coefficient of an object under examination is measured by exploiting the advantages of the synthetic aperture-type image formation method to reduce an error that appears in the attenuation coefficient due to diffusion loss internally of the object. FIGS. 5(a) and 5(b) illustrate the principle of the present invention. FIG. 5(b) shows an image following application of the synthetic aperture method, which image has already been subjected to a desired correction for attentuation. Numerals 50, 60 represent either flaws in the object or targets provided in the object beforehand.

Figure 6:
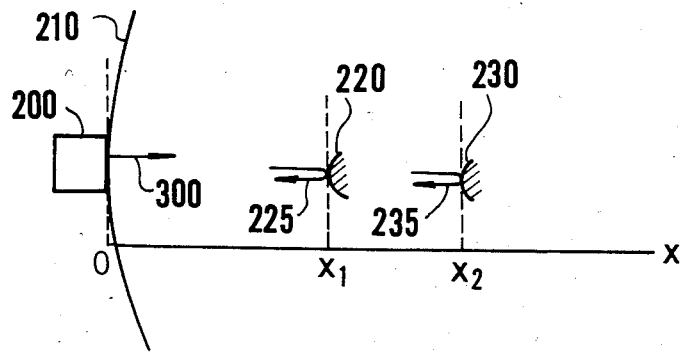
FIG. 6, FIGS. 7(a),7(b),-8(a),8(b),8(c),8(d), and FIG. 9 are views useful in describing the principle of the ultrasonic measurement method according to the present invention.

In general, when a probe 200 transmits ultrasonic pulses 300 having an intensity Io(f) and a frequency f into an object 210 under examination, as shown in FIG. 6, the intensity I(f,x) of an echo from a reflector at an interface, located at a distance X from the probe, where the acoustic impedance of the object differs is represented by the following equation:

$$I(f,x) = Io(f) \cdot G(f,x) \cdot R(f,x) \cdot D(f,x) \cdot \exp\left(-4 \int_0^x \alpha(f,x)dx\right) \quad (1)$$

where $G(f,x)$ is a term representative of diffusion caused by diffraction of the transmitted ultrasonic beam, $D(f,x)$ is a term representative of diffusion of the waves reflected by the reflector, $R(F,x)$ represents the target intensity (reflectance) of the reflector, and $\alpha(f,x)$ stands for an amplitude attenuation coefficient ascribable to plane ultrasonic wave propagation.

In order to measure the attenuation coefficient $\alpha(f,x)$ accurately, it is desirable to minimize error, namely the influence of $G(f,x)$, $D(f,x)$, $R(f,x)$ and $Io(f)$.

With the aim of excluding the aforementioned error to the greatest extent possible, the inventors have already proposed, in the specifications of Japanese Patent Application Nos. 55-49571 (Japanese Patent Application Laid-open No. 56-147082) and 58-229853 (not published as yet), respectively, a method of measuring an attenuation coefficient, which is an acoustic characteristic of the object under examination, by using ultrasonic waves of plural frequencies and submitting a plurality of echos detected through use of these frequencies to information processing, and a method of measuring an attenuation coefficient quantitatively by improving upon the former method. These methods enable an attenuation coefficient to be measured upon reducing the influence of $R(f,x)$ and $D(f,x)$.

According to these methods, however, the ultrasonic waves are assumed to be an ideal pencil beam. In other words, these methods do not take diffusion loss $G(f,x)$ experienced by the ultrasonic waves into account and therefore neglect the effects thereof.

The present invention attempts to further improve attenuation coefficient measurement accuracy by reducing measurement error ascribable to diffusion loss through use of the synthetic aperture method. More specifically, with the synthetic aperture method, rather than making the aperture (D) of the transceiving transducer sufficiently large in comparison with wavelength (λL), as in the prior art, it is necessary to use an aperture which is small in comparison with wavelength in order to form, internally of the object under examination, an ultrasonic beam having little directivity (i.e., an ultrasonic beam the directivity angle λ/D whereof is large). Accordingly, as well known, a sound field of a transmitted ultrasonic wave which emerges from an aperture small in comparison with wavelength spreads into a spherical wave as soon as it leaves the aperture. That is to say, a far sound field is formed closer to the vicinity of the probe than in the case with the conventional probe.

Figure 1:
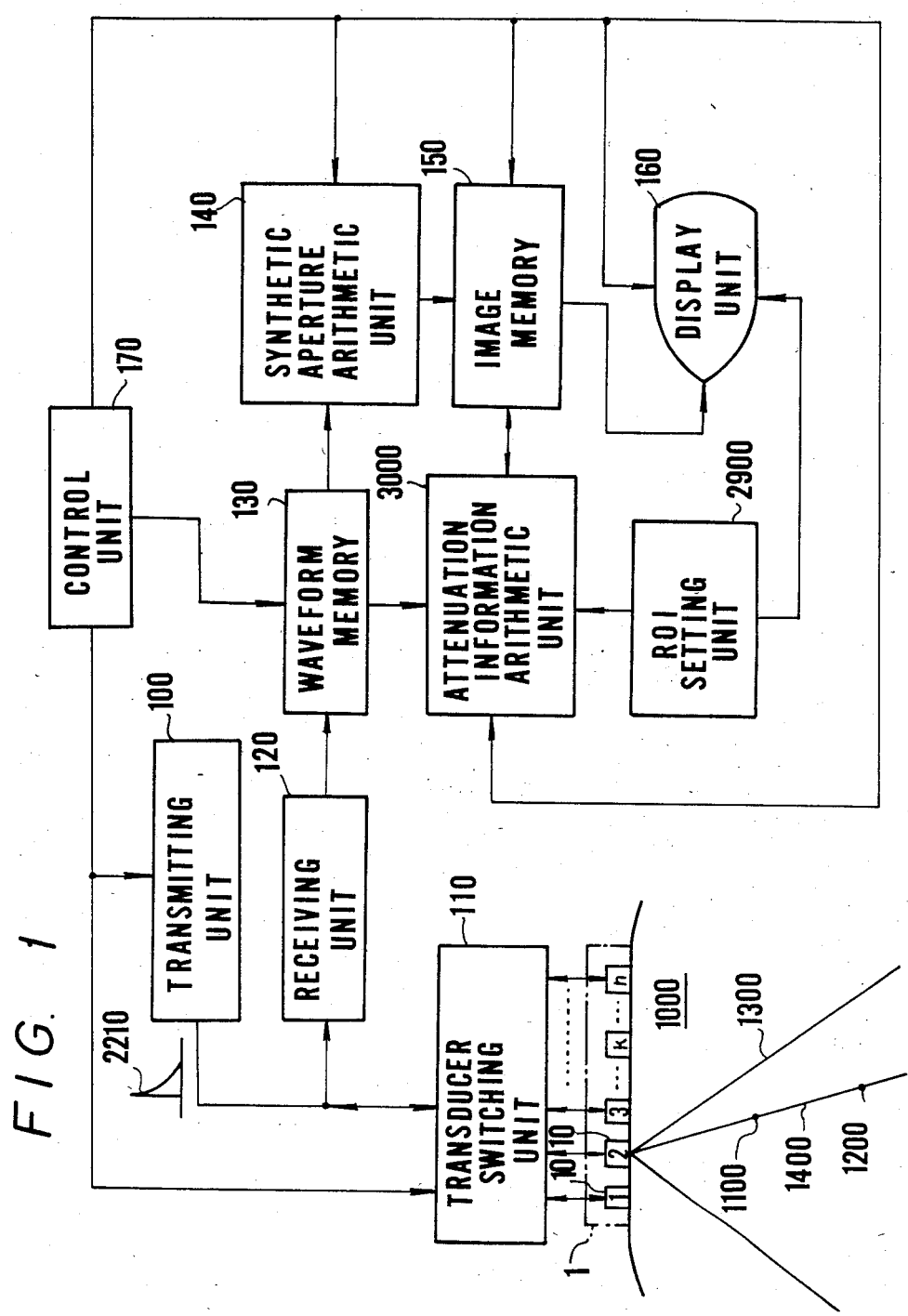
FIG. 1 is a block diagram illustrating an embodiment of an apparatus for practicing an ultrasonic measurement method according to the present invention.
Figure 2:
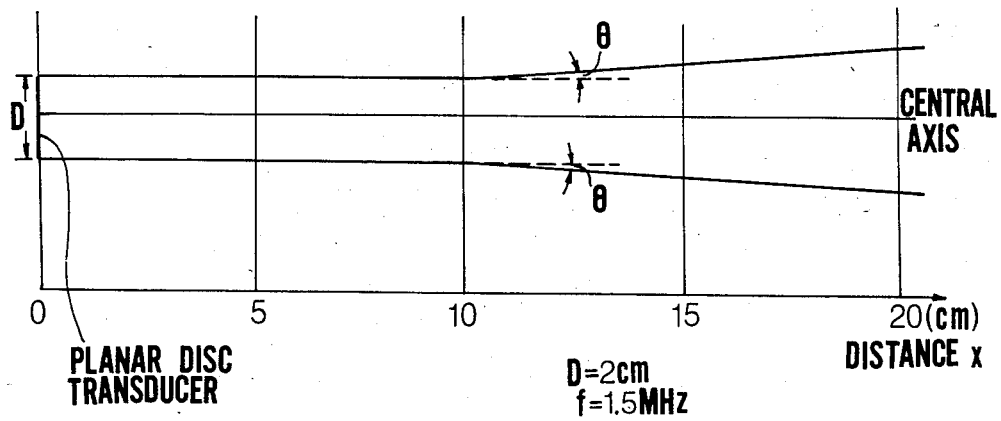
FIGS. 2(a) through 2(c) are explanatory views illustrating near and far sound fields produced by a planar disc transducer.
Figure 2:
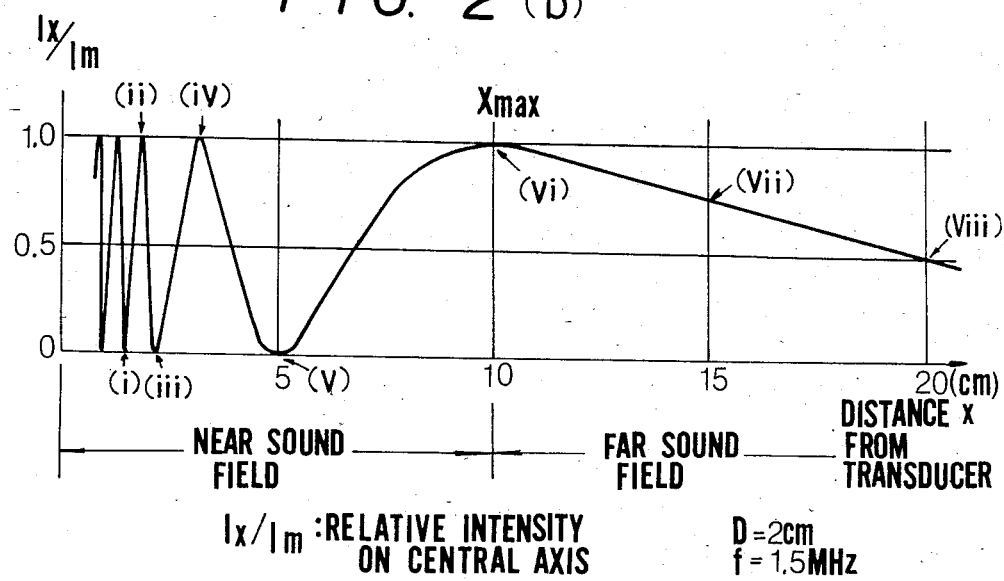
Figure 7:
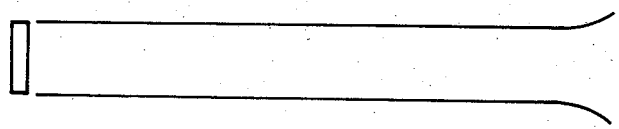
Figure 7:
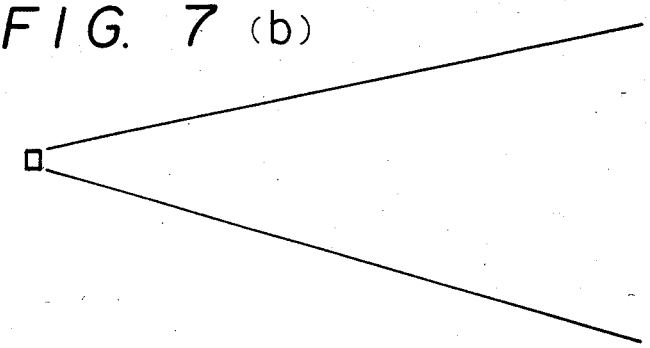

The conditions described above are shown in approximate form in FIGS. 7(a) and 7(b), in which the ultrasonic waves emerge from a planar disc transducer operating at a frequency of 3 MHz, the aperture being 10 mm in FIG. 7(a) and 1 mm in FIG. 7(b).

The intensity of a far sound field formed by a spherical wave is known to be inversely proportional to the square of the propagation distance. The foregoing facts are described in detail in chapter 2 of *Ultrasonic Material Testing* mentioned earlier. Thus, if the synthetic aperture method is applied, diffusion term can be expressed by $G(f,x)=k/x^2$, where k is a proportional constant considered to be independent of frequency within the range of frequencies used. If the substitutions $R(f,x)=g(x)\cdot f^{a(f,x)}$, $D(f,x)=x^{b(x)}$ are made, Eq. (1) can be written as follows, as set forth in the specifications of the aforementioned patent applications:

$$I(f,x) = Io(f) \cdot \frac{k}{x^2} \cdot g(x) \cdot f^{a(f,x)} \cdot x^{b(x)} \cdot \exp\left(-4\int_0^x a(f,x)dx\right) \quad (1)$$

Rearranging the above equation gives us $$I(f,x) = k \cdot Io(f) \cdot f^{a(f,x)} \cdot g(x) \cdot x^{b(x)-2} \cdot \exp\left(-4\int_0^x a(f,x)dx\right) \quad (2)$$

Taking the natural logarithm of both side of Eq. (2) results in $$\ln I(f,x) = \quad (3)$$
$$\ln kIo(f) + a(f,x)\cdot \ln f + \ln[g(x)\cdot x^{b(x)-2}] - 4\int_0^x a(f,x)dx$$

With regard to the value of a(f,x), $a(f,x)=0$ will hold at an acoustic characteristic discontinuity surface sufficiently larger than the wavelength $(\lambda = V/f)$, whereas $a(f,x)=4$ will hold at an acoustic characteristic discontinuity surface sufficiently smaller than the wavelength (where V represents the propagation velocity of sound in the object under measurement). Within a certain frequency range, therefore, a(f,x) will be constant, and the relation $0 \leq a(f,x) \leq 4$ may be considered to hold. Further, $x^{b(x)}$ may be considered as being the effect of a weakening in the reflection intensity at the position of the ultrasonic probe 200 owing to spread of the reflected wave. At a sufficiently broad acoustic characteristic discontinuity surface, $b(x)=0$ will hold, whereas $b(x)=-2$ will prevail at a small acoustic characteristic continuity surface. In general, therefore, the relation $-2 \leq b(x) \leq 0$ may be considered to hold.

When Eq. (3) is applied to the intensities of echos 225, 235 from respective reflectors 220, 230, as shown in FIG. 6, we obtain the following equations (4) and (5):

$$\ln I(f,x_1) = \quad (4)$$
$$\ln kIo(f) + a(f,x_1)\cdot \ln f + \ln[g(x_1)\cdot x_1^{b(x1)-2}] - 4\int_0^{x_1} a(f,x)dx$$

$$\ln I(f,x_2) = \quad (5)$$
$$\ln kIo(f) + a(f,x_2)\cdot \ln f + \ln[g(x_2)\cdot x_2^{b(x2)-2}] - 4\int_0^{x_2} a(f,x)dx$$

Finding the dufference between Eqs. (4) and (5) in the interval between the position $x_1$ and $x_2$ and transforming results in the following equation:

$$\int_{x_1}^{x_2} a(f,x)dx = -\frac{1}{4}\ln[I(f,x_2)/I(f,x_1)] + \frac{1}{4}[a(f,x_2) - \quad (6)$$
$$a(f,x_1)]\cdot \ln f + \frac{1}{4}\ln\{g(x_2)\cdot x_2^{b(x2)-2}\}/\{g(x_1)\cdot x_1^{b(x1)-2}\}]$$

Evaluating Eq. (6) at two frequencies $f_1$, $f_3$, taking the difference between the two values found, multiplying by $$\frac{1}{(f_3 - f_1)} \cdot \frac{1}{(x_2 - x_1)}$$

and arranging results in the following equation:

$$\frac{1}{(x_2 - x_1)\cdot(f_3 - f_1)}\int_{x_1}^{x_2}[a(f_3,x) - a(f_1,x)]dx = \quad (7)$$

$$\frac{1}{4(x_2 - x_1)\cdot(f_3 - f_1)}\ln\left[\frac{I(f_3,x_1)}{I(f_3,x_2)} \bigg/ \frac{I(f_1,x_1)}{I(f_1,x_2)}\right] +$$

$$\frac{1}{4(x_2 - x_1)\cdot(f_3 - f_1)}[\{a(f_3,x_2) - a(f_3,x_1)\}\ln f_3 -$$

$$\{a(f_1,x_2) - a(f_1,x_1)\}\ln f_1]$$

In other words, the influence of transmitted and reflected wave diffusion is eliminated by calculating the difference between the echo intensities at the two frequencies $f_1$, $f_3$. Next, we multiply by $(f_3+f_1)/2$ to arrive at the following equation:

$$H_2 = \frac{f_3 + f_1}{2(x_2 - x_1)\cdot(f_3 - f_1)}\int_{x_1}^{x_2}[a(f_3,x) - a(f_1,x)]dx = \quad (8)$$

$$\frac{f_3 + f_1}{8(x_2 - x_1)\cdot(f_3 - f_1)}\cdot \ln\left[\frac{I(f_3,x_1)}{I(f_3,x_2)} \bigg/ \frac{I(f_1,x_1)}{I(f_1,x_2)}\right] + D_2$$

where $$D_2 = \frac{f_3 + f_1}{8(x_2 - x_1)\cdot(f_3 - f_1)}[\{a(f_3,x_2) - a(f_3,x_1)\}\ln f_3 -$$

$$\{a(f_1,x_2) - a(f_1,x_1)\}\ln f_1]$$

If we assume that $a(f,x) = a_o(x)f^{\beta(x)}$ holds, the left side of Eq. (8) can be transformed to $$\frac{f_3 + f_1}{2(x_2 - x_1)\cdot(f_3 - f_1)}\int_{x_1}^{x_2}[a(f_3,x) - a(f_1,x)]dx =$$

$$\frac{f_3 + f_1}{2(x_2 - x_1)(f_3 - f_1)}\int_{x_1}^{x_2}a_o(x)[f_3^{\beta(x)} - f_1^{\beta(x)}]dx$$

Since we may also write the following:

$$a(f_3,x) \approx a(f_1,x) + (f_3 - f_1)\left\{\frac{\partial}{\partial f}a(f,x)\right\}\bigg|_{f = \frac{f_1 + f_3}{2}} =$$

-continued
$$a(f_1, x) + \frac{2\beta(x)(f_3 - f_1)}{f_1 + f_3} \cdot a_o(x) \cdot \left(\frac{f_1 + f_3}{2}\right)^{\beta(x)}$$

we will obtain $$H_2 \approx \frac{1}{x_2 - x_1} \int_{x_1}^{x_2} \beta(x) \cdot a\left(\frac{f_1 + f_3}{2}, x\right) dx \quad (9)$$

Thus, Eq. (9) gives, in approximate form, a value obtained by multiplying $$a\left(\frac{f_1 + f_3}{2}, x\right),$$

at the average value $$\left(\frac{f_1 + f_3}{2}\right)$$

of the frequencies $f_1$, $f_3$ between $x_1$ and $x_2$, by the coefficient $\beta(x)$, which is representative of frequency dependence of the attenuation coefficient. Futher, using data regarding three frequencies $f_1$, $f_2$, $f_3$, ($f_1 < f_2 < f_3$), we take a diffrence quotient of second order with relation to the frequency logarithms $\ln f_1$, $\ln f_2$, $\ln f_3$, and make a transformation to obtain the following equation:

$$H_3 = \frac{A}{x_2 - x_1} \int_{x_1}^{x_2} [a(f_1,x) \cdot \ln(f_2/f_3) + a(f_2,x) \cdot \ln(f_3/f_1) + \quad (10)$$

$$a(f_3,x) \cdot \ln(f_1/f_2)]dx$$

$$= \frac{-A}{4(x_2 - x_1)} \cdot \left\{ \ln \frac{I(f_1,x_2)}{I(f_1,x_1)} \cdot \ln(f_2/f_3) + \right.$$

$$\left. \ln \frac{I(f_2,x_2)}{I(f_2,x_1)} \cdot \ln(f_3/f_1) + \ln \frac{I(f_3,x_2)}{I(f_3,x_1)} \cdot \ln(f_1/f_2) \right\} + D_3$$

$$D_3 = \frac{-A}{4(x_2 - x_1)} [\{a(f_1,x_2) - a(f_1,x_1)\} \cdot \ln f_1 \cdot \ln(f_2/f_3) +$$
$$\{a(f_2,x_2) - a(f_2,x_1)\} \cdot \ln f_2 \cdot \ln(f_3/f_1) +$$
$$\{a(f_3,x_2) - a(f_3,x_1)\} \ln f_3 \cdot \ln(f_1/f_2)]$$

and
$$A = 2/\{\ln(f_1/f_2) \cdot \ln(f_2/f_3) \cdot \ln(f_1/f_3)\}$$

A mathematical discussion of the process for obtaining Eq. (10) is set forth in detail for a pencil beam in our Japanese Patent Application No. 58-229853 (not published as yet) (for which the corresponding applications in the USA and Europe are U.S. Ser. No. 657,028 and EPA 84 112 223.7, respectively).

Returning to $H_3$, we may write $$H_3 \approx \frac{1}{x_2 - x_1} \cdot \int_{x_1}^{x_2} \beta^2(x) \cdot a\left(\frac{f_1 + f_2 + f_3}{3}, x\right) dx \quad (11)$$

Thus, Eq. (11) gives, in approximate form, a value obtained by multiplying $$\left(\frac{f_1 + f_2 + f_3}{3}, x\right),$$

at the average value $$\frac{f_1 + f_2 + f_3}{3}$$

of the frequencies $f_1$, $f_2$, $f_3$ between $x_1$ and $x_2$, by the square of (x).

Dividing Eq. (11) by Eq. (9) gives us $$H_3/H_2 \approx \int_{x_1}^{x_2} \beta^2(x) \cdot a\left(\frac{f_1 + f_2 + f_3}{3}, x\right) dx / \int_{x_1}^{x_2} \beta^2(x) \cdot \quad (12)$$

$$a\left(\frac{f_1 + f_3}{2}, x\right) dx$$

Thus, Eq. (12) gives an approximate expression of the mean value of $\beta(x)$ between $x_1$ and $x_2$ and between $f_1$ and $f_3$. $H_3/H_2$ takes on the following form from Eq. (10):

$$H_3/H_2 = \frac{\frac{-A}{4(x_2 - x_1)} \left[ \ln \frac{I(f_1,x_2)}{I(f_1,x_1)} \cdot \ln \frac{f_2}{f_3} + \ln \frac{I(f_2,x_2)}{I(f_2,x_1)} \cdot \ln \frac{f_3}{f_1} + \ln \frac{I(f_3,x_2)}{I(f_3,x_1)} \cdot \ln \frac{f_1}{f_2} \right] + D_3}{\frac{f_3 + f_1}{8(x_2 - x_1)(f_3 - f_1)} \cdot \ln \left[ \frac{I(f_3,x_1)}{I(f_3,x_2)} / \frac{I(f_1,x_1)}{I(f_1,x_2)} \right] + D_2} \quad (13)$$

Where $$D_3 = -\frac{A}{4(x_2 - x_1)} \left[ \{a(f_1,f_2) - a(f_1,x_1)\} \cdot \ln f_1 \cdot \ln(f_2/f_3) + \right.$$

$$\left. \{a(f_2,x_2) - a(f_2,x_1)\} \cdot \ln f_2 \cdot \ln\left(\frac{f_3}{f_1}\right) + \{a(f_3,x_2) - a(f_3,x_1)\} \cdot \ln f_3 \cdot \ln\left(\frac{f_1}{f_2}\right) \right]$$

$$D_2 = \frac{f_3 + f_1}{8(x_2 - x_1) \cdot (f_3 - f_1)} [\{a(f_3,x_2) - a(f_3,x_1)\} \cdot \ln f_3 - \{a(f_1,x_2) - a(f_1,x_1)\} \cdot \ln f_1]$$

where

Further, from Eqs. (11) and (9) we have:

$$(H_2)^2/H_3 \approx \left\{\int_{x_1}^{x_2} \beta(x) \cdot a\left(\frac{f_1+f_2}{2}, x\right) dx\right\}^2 / \int_{x_1}^{x_2} \beta^2(x) \cdot a\left(\frac{f_1+f_2+f_3}{3}, x\right) dx \quad (14)$$

Thus, Eq. (14) gives a mean value of $\alpha(f,x)$ between $x_1$ and $x_2$ and between $f_1$ and $f_3$. $(H_2)^2/H_3$ takes on the following form from Eqs. (8), (10):

$$(H_2)^2/H_3 = \frac{\left\{\frac{f_3+f_1}{8(x_2-x_1)(f_3-f_1)} \cdot \ln\left[\frac{I(f_3,x_1)}{I(f_3,x_2)} / \frac{I(f_1,x_1)}{I(f_1,x_2)}\right] + D_2\right\}^2}{\frac{-A}{4(x_2-x_1)}\left[\ln\frac{I(f_1,x_2)}{I(f_1,x_1)}\ln\left(\frac{f_2}{f_3}\right) + \ln\frac{I(f_2,x_2)}{I(f_2,x_1)}\ln\left(\frac{f_3}{f_1}\right) + \ln\frac{I(f_3,x_2)}{I(f_3,x_1)} \cdot \ln\left(\frac{f_1}{f_2}\right)\right] + D_3} \quad (15)$$

The first term in the denominator of Eq. (13) and the first term in the numerator thereof are measured quantities, but the second terms, namely $D_2$ and $D_3$, arise owing to frequency dependence ascribable to the intensity of reflection at the surface of acoustic characteristic discontinuity. These represent error terms with respect to $\beta(x)$. If the coefficient $a(f,x)$ of the frequency dependence $f^{a(f,x)}$ of the reflection intensity is constant within the range of frequencies measured, namely if $a(f_1,x_1)=a(f_2,x_1)=a(f_3,x_1)\equiv a(x_1)$ and $a(f_1,x_2)=a(f_2,x_2)=a(f_3,x_2)\equiv a(x_2)$ hold, then $a(f,x)$ will be a function solely of x and $D_3$ will be zero. Accordingly, Eqs. (8), (10) may then be written as follows:

$$H_2 = \frac{f_3+f_1}{2(x_2-x_1)\cdot(f_3-f_1)} \int_{x_1}^{x_2}[\alpha(f_3,x)-\alpha(f_1,x)]dx \quad (16)$$

$$= \frac{f_3+f_1}{8(x_2-x_1)\cdot(f_3-f_1)} \cdot \ln\left[\frac{I(f_3,x_1)}{I(f_3,x_2)} / \frac{I(f_1,x_1)}{I(f_1,x_2)}\right] +$$

$$\frac{f_3+f_1}{8(x_2-x_1)\cdot(f_3-f_1)}\left[\{a(x_2)-a(x_1)\}\cdot\ln\left(\frac{f_3}{f_1}\right)\right]$$

$$H_3 = \frac{-A}{4(x_2-x_1)}\left(\ln\frac{I(f_1,x_2)}{I(f_1,x_1)} \cdot \ln\left(\frac{f_2}{f_3}\right) + \ln\frac{I(f_2,x_2)}{I(f_2,x_1)} \cdot \ln\left(\frac{f_3}{f_1}\right) + \ln\frac{I(f_3,x_2)}{I(f_3,x_1)} \cdot \ln\left(\frac{f_1}{f_2}\right)\right) \quad (17)$$

$$(\because D_3 = 0)$$

Therefore Eq. (13) takes on the following from from Eqs. (16) and (17):

$$\beta(x) \approx H_3/H_2 = \frac{-2A(f_3-f_1)\left[\ln\frac{I(f_1,x_2)}{I(f_1,x_1)}\ln\left(\frac{f_2}{f_3}\right) + \ln\frac{I(f_2,x_2)}{I(f_2,x_1)}\ln\left(\frac{f_3}{f_1}\right) + \ln\frac{I(f_3,x_2)}{I(f_3,x_1)} \cdot \ln\left(\frac{f_1}{f_2}\right)\right]}{(f_3+f_1)\cdot\left[\ln\left\{\frac{I(f_3,x_1)}{I(f_3,x_2)} / \frac{I(f_1,x_1)}{I(f_1,x_2)}\right\} + (a(x_2)-a(x_1))\cdot\ln\left(\frac{f_3}{f_1}\right)\right]} \quad (18)$$

And Eq. (15) takes on the following form from Eqs. (16) and (17):

$$a(f,x) = \frac{(H_2)^2}{H_3} = -\frac{1}{16A}\left[\frac{f_3+f_1}{(x_2-x_1)\cdot(f_3-f_1)}\right]^2 \quad (19)$$

$$\frac{\left\{\ln\left[\frac{I(f_3,x_1)}{I(f_3,x_2)} / \frac{I(f_1,x_1)}{I(f_1,x_2)}\right] + (a(x_2)-a(x_1))\cdot\ln\left(\frac{f_3}{f_1}\right)\right\}^2}{\left\{\ln\frac{I(f_1,x_2)}{I(f_1,x_1)} \cdot \ln\left(\frac{f_2}{f_3}\right) + \ln\frac{I(f_2,x_2)}{I(f_2,x_1)} \cdot \ln\left(\frac{f_3}{f_1}\right) + \ln\frac{I(f_3,x_2)}{I(f_3,x_1)} \cdot \ln\left(\frac{f_1}{f_2}\right)\right\}}$$

It may be understood that these two equations have fewer error terms in comparison with Eqs. (13) and (15). More specifically, the error term in Eq. (18) is solely $[a(x_2)-a(x_1)]\cdot\ln(f_3/f_1)$ in the denominator, and the error term in Eq. (19) is solely $[a(x_2)-a(x_1)]\cdot\ln(f_3/f_1)$ in the numerator.

If the coefficient $a(x)$ of the frequency dependence $f^{a(x)}$ of the reflection intensity is constant and independent of the distance x, then, from $a(x_2)=a(x_1)$, Eq. (18) may be written as the following equation, in which the error is reduced even further:

$$\beta(x) \approx H_3/H_2 = -2A \frac{(f_3-f_1)\left[\ln\frac{I(f_1,x_2)}{I(f_1,x_1)}\ln\left(\frac{f_2}{f_3}\right) + \ln\frac{I(f_2,x_2)}{I(f_2,x_1)} \cdot \ln\left(\frac{f_3}{f_1}\right) + \ln\frac{I(f_3,x_2)}{I(f_3,x_1)} \cdot \ln\left(\frac{f_1}{f_2}\right)\right]}{(f_3+f_1) \times \ln\left[\frac{I(f_3,x_1)}{I(f_3,x_2)} / \frac{I(f_1,x_1)}{I(f_1,x_2)}\right]} \quad (20)$$

In other words, if the coefficient $a(f,x)$ indicating the frequency dependence of the reflection intensity is constant and independent of the frequency f within the measured range and of the distance x, then $a(f,x)=a$ will hold and, in accordance with Eq. (20), the means value $\beta(x)$ of the frequency dependence of the attenuation coefficient $\alpha(f,x)$ can be measured with even greater accuracy. In this case, in accordance with Eq. (19), it is also possible to measure $\alpha(f,x)$ with greater accuracy as shown by the following equation:

$$\alpha(f,x) = -\frac{1}{16A}\left[\frac{f_3+f_1}{(x_2-x_1)(f_3-f_1)}\right]^2 \times \frac{\left[\ln\frac{I(f_3,x_1)}{I(f_3,x_2)}\Big/\frac{I(f_1,x_1)}{I(f_1,x_2)}\right]^2}{\left[\ln\frac{I(f_1,x_2)}{I(f_1,x_1)}\cdot\ln\left(\frac{f_2}{f_3}\right) + \ln\frac{I(f_2,x_2)}{I(f_2,x_1)}\cdot\ln\left(\frac{f_3}{f_1}\right) + \ln\frac{I(f_3,x_2)}{I(f_3,x_1)}\cdot\ln\left(\frac{f_1}{f_2}\right)\right]} \tag{21}$$

In this case, $\alpha_o(x)$ also is obtained with greater accuracy from the relation $\alpha_o(x)=\alpha(f,x)/f^{\beta(x)}$.

In Eqs. (8), (10), $D_2$ and $D_3$ are error terms which cannot be found from experimental values. In Eq. (8) $D_2$ vanishes when $a(f,x)$ is constant and independent of $f_1$, $f_3$, $x_1$, $x_2$. In Eq. (10), $D_3$ vanishes when $a(f,x)$ is constant with regard to the frequencies $f_1$, $f_2$, $f_3$ even if it is dependent upon $x_1$, $x_2$. In cases where the foregoing conditions do not hold, however, the relative error can be evaluated in the following way. Specifically, since $0 \leq a(f,x) \leq 4$ holds, we may write $$\left|\frac{D_2}{H_2}\right| \leq \tag{22}$$

$$\frac{f_3+f_1}{2|f_3-f_1|}|\ln(f_3/f_1)|/\int_{x_1}^{x_2}\beta(x)\cdot\alpha\left(\frac{f_1+f_3}{2},x\right)dx$$

This gives the relative error ascribable to $D_2$ in Eq. (8). Likewise, we have $$|D_3/H_3| \leq \frac{2\text{Max}[\,|\ln f_1\cdot\ln(f_2/f_3)|\,,\,|\ln f_3\cdot\ln(f_1/f_2)|\,]}{\left|\int_{x_1}^{x_2}\beta^2(x)\alpha\left(\frac{f_1+f_2+f_3}{3},x\right)dx\right|\cdot|\ln(f_1/f_2)\ln(f_2/f_3)\ln(f_1/f_3)|} \tag{23}$$

This gives the relative error ascribable to $D_3$ in Eq. (10). In conclusion, the error terms $D_2$, $D_3$ can be neglected if, from Eqs. (22), (23), the values of the following are sufficiently large:

$$\int_{x_1}^{x_2}\beta(x)\cdot\alpha\left(\frac{f_1+f_3}{2},x\right)dx;$$

$$\int_{x_1}^{x_2}\beta^2(x)\cdot\alpha\left(\frac{f_1+f_2+f_3}{3},x\right)dx$$

In such case, Eqs. (8), (10) can be transformed as follows:

$$H_2 \approx \frac{f_3+f_1}{8(x_2-x_1)\cdot(f_3-f_1)}\cdot\ln\left[\frac{I(f_3,x_1)}{I(f_3,x_2)}\Big/\frac{I(f_1,x_1)}{I(f_1,x_2)}\right] \tag{8'}$$

$$H_3 = \frac{-A}{4(x_2-x_1)}\left\{\ln\frac{I(f_1,x_2)}{I(f_1,x_1)}\cdot\ln(f_2/f_3) + \ln\frac{I(f_2,x_2)}{I(f_2,x_1)}\cdot \right. \tag{10'}$$

$$\left. \ln(f_3/f_1) + \ln\frac{I(f_3,x_2)}{I(f_3,x_1)}\cdot\ln(f_1/f_2)\right\}$$

As set forth above, plan ultrasonic wave pulses having three different frequencies $f_1$, $f_2$, $f_3$ are inflicted upon the object under examination and the object's attenuation coefficinets $\alpha(f,x)$, $\alpha_o(x)$ and their frequency dependence $\beta(x)$ can be approximately measured based on the resulting echo signals. In particular, if the reflection intensity is constant and independent of the observed range of frequency f and of the distance x, then it is possible to measure $\alpha(f,x)$, $\alpha_o(f,x)$ and $\beta(x)$ with greater accuracy.

Thus we can sum up by saying that the coordinate values of each scatterer (flaw) in the object relative to each transducer are known from a two-dimensional distribution of the scatters, which distribution is obtained by the ultrasonic measurement apparatus of FIG. 4 that uses the conventional synthetic aperture method.

Let us now discuss direct application of the above-described echo intensity processing method to the synthetic aperture method of FIG. 5(a) and (b).

FIG. 5(b) shows the reconstructed image, in which numerals 50, 60 represent reflectors corresponding to the reflectors 220, 230, respectively, of FIG. 6. To find the attenuation coefficient between the reflectors 50 and 60, we find a straight line 80 connecting the points where the reflectors 50, 60 are located and extend the straight line to the probe side so that the extension will intersect the row of n transducers (1~n) constituting the probe 1, as shown in FIG. 5(a). Now we find the transducer nearest the point of intersection, which in the example of FIG. 5(a) is the fifth transducer from the left. Next, an echo signal (the original signal, namely the signal that prevails prior to processing for, e.g., correction of attenuation) 500 (shown in FIG. 5(c)) detected by this fifth transducer is extracted from the waveform memory 130 in the apparatus of FIG. 4. The echo signal 500 contains echo signals 510, 520 corresponding to the reflectors 50, 60, respectively. That is, $I(f,x_1)$ in Eq. (4) represents the intensity of the signal 510, and $I(f,x_2)$ in Eq. (5) corresponds to the intensity of the signal 520. $I_o(f)$ may be considered to be the intensity of ultrasonic waves transmitted in the direction of the reflectors 50, 60.

By applying the processing method described in detail above, the values of $\alpha(f,x)$, $\alpha_o(x)$, $\beta(x)$ relating to the attenuation coefficient between the reflectors 50, 60 can be measured approximately via Eqs. (18), (19) or more accurately via Eqs. (20), (21), based on the nature and attenuation of each of these reflectors.

FIGS. 8(a) through 8(d) illustrate a situation which is more complicated than that shown in FIGS. 5(a) and 5(b), as the object under examination in this case contains a third reflector 90 in addition to the reflectors 50 and 60. Moreover, the reflectors 60 and 90 are equidistant as seen from the fifth transducer. As a consequence, the echo signals from the reflectors 60, 90 mix in the echo signal output 500 (shown in FIG. 8(c)) of the fifth transducer within an identical reception time period and are measured as an echo signal 530.

Whether or not the reflector 90 is located at the same distance from the fifth transducer as the reflector 60 can be determined in advance from the reproduced image (shown in FIG. 8(b)), as will be described in detail below. In this case, therefore, a straight line 100 connecting the reflectors 90, 50 is extended toward the probe 1 and intersects the seventh transducer 7. Accordingly, information relating to the attenuation coefficient between the reflectors 90, 50 can be obtained by performing signal processing similar to that described above, wherein $I(f,x_1)$, $I(f,x_2)$ will represent signals 710, 720 (shown in FIG. 8(d)) from the reflectors 50, 90, respectively, these signals being contained in an echo signal 700 from the seventh transducer.

Thus it has been shown, as set forth above, that information relating to the attenuation coefficient of an object not heretofore obtainable with the conventional method and not even with the synthetic aperture method can be acquired through correct measurement by expanding upon the signal processing method disclosed in the specification of the present applicant's previously filed Japanese Patent Application No. 55-49571 (Japanese Patent Application Laid-open No. 56-147082), and by applying this method to the synthetic aperture method, and that this can be achieved without introducing large errors due to transmitted sound field diffusion loss, as occurs in the prior art, and without going to the trouble of compensating for diffusion loss by means of a reference specimen for attenuation measuring purposes. It should be noted that the present invention is not limited to ultrasonic flaw detection but can also be applied to liquid specimens for which the attenuation coefficient is unknown. Such an application can readily be practiced by adopting a liquid as the object 2 shown in FIG. 5(a) and disposing the reflectors 50, 60, which would be plastic rods or the like, within the liquid.

Figure 8:
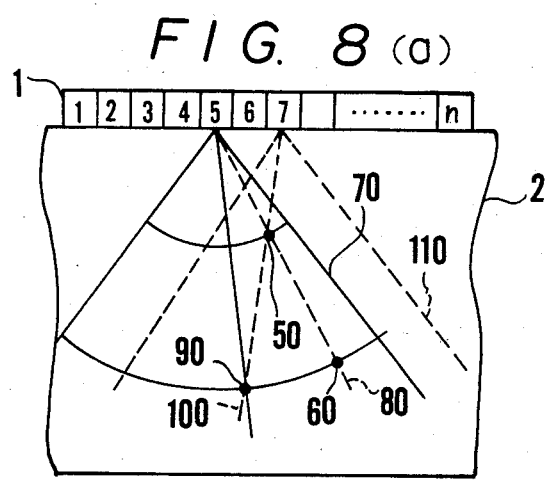
Figure 8:
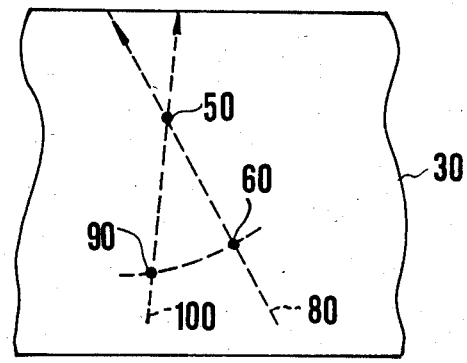
Figure 8:
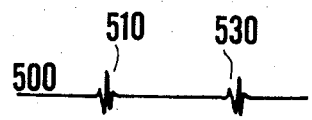
Figure 8:
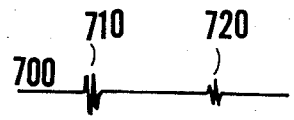

As for application of the present invention to an ultrasonic diagnostic system for medical purposes, namely to measurement of living tissue, it will be appreciated that a more sophisticated method of signal processing will be required in view of the fact that such tissue does not possess a simple constitution of the type shown in FIG. 5(a) or FIG. 8(a) but may instead be thought of as a fairly complex assemblage of scatterers.

Figure 9:
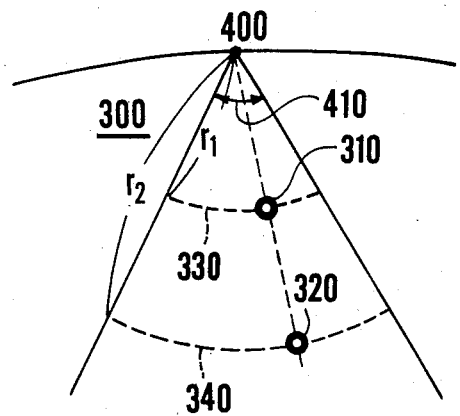

However, analysis is comparatively easy if we imagine a case where, as shown in FIG. 9, a liver 300 contains, internally thereof, comparatively stout blood vessels 310 and 320 as reflectors corresponding to the reflector shown in FIGS. 3 and 4. In such case, the echo signal intensity received will be a mixture of (a) intensities exhibited by echo signals from reflectors on an arc 330 within a directivity angle 410, the radius of the arc being the distance $r$ ($=r_1$) from a transmission acoustic source 400 to the reflector 310, and (b) the intensity exhibited by an echo signal from the reflector 310. The same will hold true for the reflector 320.

Referring to Eq. (2), let us assume that the intensity of the echo signal from the reflector 310 is expressed by $I(f,r_1)$, and that the sum of the intensities of the echo signals from the other reflectors on the arc 330 is expressed by $I'(f,r_1)$. We may then express the intensity $J(f,r_1)$ of the echo signal received by the transducer 400 as follows:

$$J(f,r_1) = I(f,r_1) + I'(f,r_1) = I(f,r_1)\left[1 + \frac{I'(f,r_1)}{I(f,r_1)}\right] \quad (24)$$

$I'(f,r_1)$ is expressed by the following equation:

$$I'(f,r_1) = \quad (25)$$

$$kI_0(f) \cdot f^{a'(f,r_1)} \cdot g'(r_1) \cdot r_1^{b'(r_1)-2} \cdot \exp\left(-4\int_0^{r_1} \alpha'(f,r)dr\right)$$

Here we assume that the intensity of the transmitted ultrasonic wave is $I_0(f)$, which is constant within the directivity angle 410. From Eqs. (2) and (25), Eq. (24) becomes:

$$J(f,r_1)$$

$$= KI_0(f)\left\{f^{a(f,r_1)} \cdot g(r_1) \cdot r_1^{b(r_1)-2} \cdot \exp\left(-4\int_0^{r_1} \alpha(f,r)dr\right) + \right. \quad (26)$$

$$\left. f^{a'(f,r_1)} \cdot g'(r_1) \cdot r_1^{b'(r_1)-2} \cdot \exp\left(-4\int_0^{r_1} \alpha'(f,r)dr\right)\right\}$$

$$= KI_0(f) \cdot f^{a(f,r_1)} \cdot g(r_1) \cdot r_1^{b(r_1)-2} \cdot \exp\left(-4\int_0^{r_1} \alpha(f,r)dr\right) \times \quad (27)$$

$$\left[1 + \frac{f^{a'(f,r_1)}}{f^{a(f,r_1)}} \cdot \frac{g'(r_1)}{g(r_1)} \cdot \frac{r_1^{b'(r_1)}}{r_1^{b(r_1)}} \exp\left(4\int_0^{r_1} [\alpha'(f,r) - \alpha(f,r)]dr\right)\right]$$

Taking the natural logarithm of both sides of Eq. (27) gives us $$\ln J(f,r_1) = \ln KI_0(f) + a(f,r_1) \cdot \ln f + \ln[g(r_1) \cdot r_1^{b(r_1)-2}] - \quad (28)$$

$$4\int_0^{r_1} \alpha(f,r)dr + \ln\left[1 + \frac{f^{a'(f,r_1)}}{f^{a(f,r_1)}} \cdot \frac{g'(r_1)}{g(r_1)} \cdot \frac{r^{b'(r_1)}}{r^{b(r_1)}} \cdot \right.$$

$$\left. \exp\left(4\int_0^{r_1} \{\alpha'(f,r) - \alpha(f,r)\}dr\right)\right]$$

The last term on the right side of the above equation is an error term which, in comparison with Eq. (2), is caused by the presense of reflectors other than the reflector 310 on the arc 330.

Accordingly, we will assume that the reflection intensity of the reflector 310 is sufficiently large in comparison with the reflection intensities of the other reflectors on the arc 330. That is, we will assume that the following condition holds:

$$f^{a(f,r_1)} \cdot g(r_1) >> f^{a'(f,r_1)} \cdot g'(r_1) \tag{29}$$

Further, assuming that the reflectors (with the exception of reflector 310) on the arc 330 are sufficiently small in comparison with wavelength, $b'(r_1) = -2$ may be considered to hold for these reflectors and $-2 < b(r_1) < 0$ for the reflector 310, so that we have:

$$r_1{}^{b'(r_1)}/r_1{}^{b(r_1)} = 1/r_1{}^{b(r_1)+2} < 1, \text{ for } r_1 > 1,$$

since $0 < b(r_1) + 2 < 2$ holds.

Since $\alpha'(f,r) - \alpha(f,r)$ may be considered to hold for a liver, which is one example of living tissue, the value of $$\int_0^{r_1} [\alpha'(f,r) - \alpha(f,r)]dr$$

is presumed to be $|\Delta\alpha|$, which is very small. Therefore, if the error term in Eq. (28) is replaced by $E(f,r_1)$, we may write $$E(f,r_1) = \ln\left[1 + \frac{f^{a'(f,r_1)}g'(r_1)}{f^{a(f,r_1)}g(r_1)} \cdot \frac{1}{r_1{}^{b(r_1)+2}} \exp(|\Delta\alpha|)\right] \tag{30}$$

and if $\exp(|\Delta\alpha|) \simeq 1$ is considered to hold, Eq. (30) reduces to $$E(f,r_1) = \ln\left[1 + \frac{f^{a'(f,r_1)}g'(r_1)}{f^{a(f,r_1)}g(r_1)} \cdot \frac{1}{r_1{}^{b(r_1)+2}}\right] \tag{31}$$

Accordingly, assuming from the condition set forth in Eq. (29) that the second term enclosed by the brackets in Eq. (31) is assumed to be very small, namely that the condition $$\frac{f^{a'(f,r_1)}g'(r_1)}{f^{a(f,r_1)}g(r_1)} \cdot \frac{1}{r_1{}^{b(r_1)+2}} << 1$$

holds, then Eq. (31) will reduce to $$E(f,r_1) \simeq n(1) = 0$$

so that the error term may be considered to be negligibly small. The foregoing will also hold true for the reflector 320, so that we will have $E(f,r_2) \simeq 0$. Subsequent processing is as already set forth in detail above, enabling the acquistion of information relating to the attenuation coefficient between the reflectors 310, 320. Thus, by posing specific assumptions, the method of the present invention can also be applied to measurement of living tissue.

Figure 11:
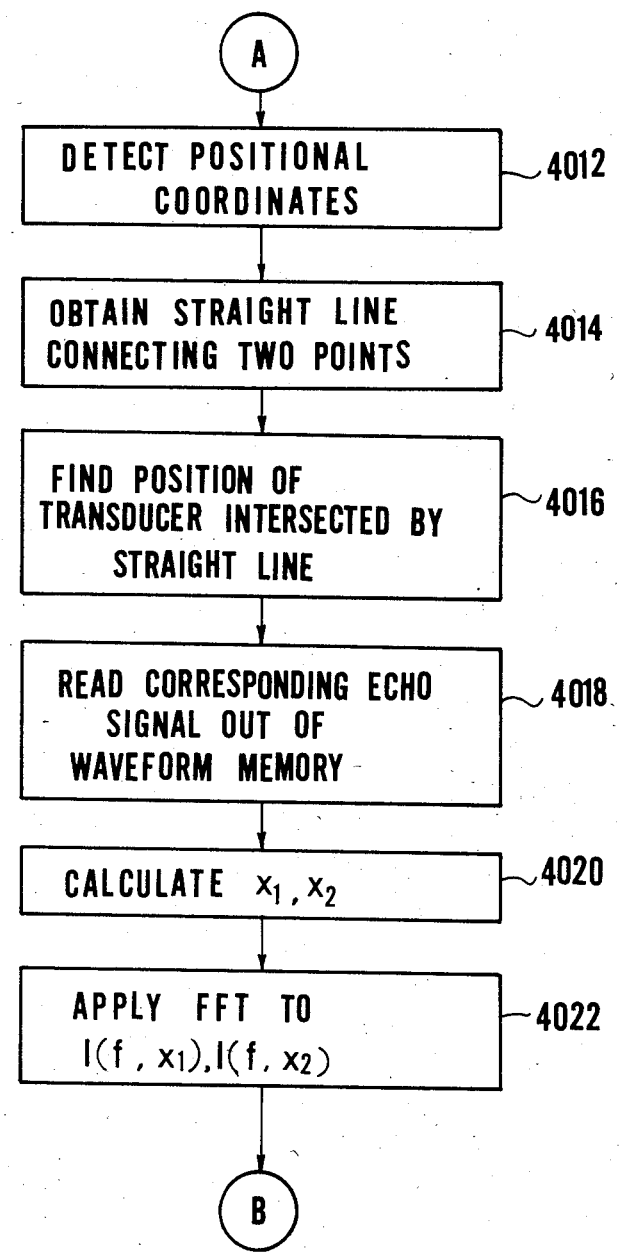
FIGS. 11(a) and 11(b) and 11(c) are flowcharts illustrating the operation of the embodiment shown in FIG. 1.

Let us now give a detailed description of an embodiment of the present invention, which is illustrated in the block diagram of FIG. 1, with reference to the flowcharts of FIGS. 11(a) through 11(c) which show control procedures executed by the control unit 170. The apparatus of FIG. 1 is distinguishable over the prior-art apparatus of FIG. 4 mainly by provision of an attenuation information arithmetic unit 3000 and a region-of-interest setting unit 2900.

Figure 10:
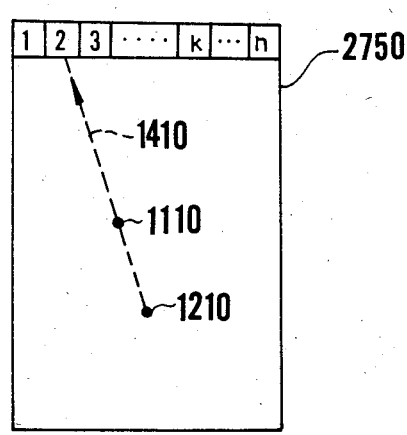
FIGS. 10(a) and 10(b) are views for describing the operation of the embodiment shown in FIG. 1.
Figure 10:
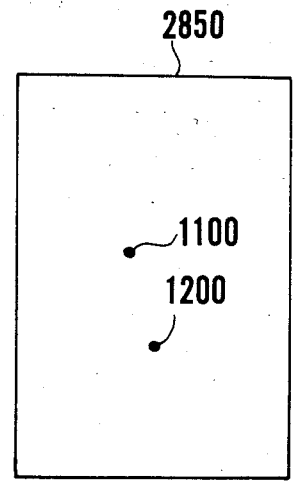

With reference now to the flowcharts, the loop consisting of steps 4000 through 4004 calls for transmitting an ultrasonic pulse into an object 1000 under examination sequentially from the first to the n-th transducers of the probe 1, and sequentially storing the echo signals received by the transducers in the waveform memory 130. When echo signals from all of the transducers have been stored in the waveform memory 130 (step 4004), the next step executed is a step 4006, which calls for setting the synthetic aperture arithmetic unit 140 into operation to perform an image reconstruction by means of the synthetic aperture method. The reconstructed image is stored in the image memory 150. The image signal stored in the image memory 150 is subjected to an arbitrary attenuation correction and is brightness-modulated for display as an image 2850 [FIG. 10(b)] on the display unit 160. This is step 4008 of the flowchart.

It is assumed here that two flaws 1100, 1200 appear in the image 2850. In this case, the flaws 1100, 1200 can be made to show up clearly in the image 2850 arbitrarily corrected for attenuation. Next, at a step 4010, the region-of-interest setting unit 2900 is manipulated to set a region which contains the flaws 1100, 1200. The setting unit 2900 may be comprise, e.g., a light pen, in which case the light pen would be used to designate the two flaws 1100, 1200 to obtain the coordinates of the positions at which the flaws 1100, 1200 are located on the image 2850. A flaw position recognition operation of this kind can also be performed automatically within a set region by the attenuation information arithmetic unit 3000.

Whichever method of setting the region of interest is adopted, the attenuation information arithmetic unit 3000 executes a step 4012 to convert the coordinates of the two flaws 1100, 1200 on the displayed image 2850 into position information contained in image data 2750 stored in the image memory 150. The image data 2750 may be thought of as having the form shown in FIG. 10(a) when expressed in terms of assumed two-dimensional space. Next, at a step 4014, a straight line connecting the two flaws 1100, 1200 in the assumed space is obtained from the information indicative of the flaw positions. This is followed by a step 4016, at which the straight line 1410 is extended and the number of the transducer closest to the point at which the extension intersects the straight line connecting all of the transducers is obtained.

Next, at a step 4018, the echo signal received by the transducer determined at the step 4016 is read out of the wave memory 130, which stores the echo signals from all transducers as mentioned above. The read echo signal may be thought of as corresponding to the signal 500 in FIG. 5(a). The distance from the abovementioned transducer to each of the two flaws is calculated at a step 4020, with the distances obtained being designated $X_1$, $X_2$. A fast-Fourier transformation (FFT) is applied at a step 4022 to the echo signal intensities $I(f,X_1)$, $I(f,X_2)$ corresponding to the respective distances $X_1$, $X_2$, and $I(f_1,X_1)$, $I(f_2,X_1)$, $I(f_3,X_1)$, $I(f_1,X_2)$, $I(f_2,X_2)$, $I(f_3,X_2)$ are obtained at a step 4024.

Steps 4026 through 4034 call for finding $H_2$, $H_3$, $\beta(x)$, $\alpha(f,x)$ and $\alpha_o(x)$ in succession. Next, at a step 4036, the values of $\beta(x)$, $\alpha(f,x)$ and $\alpha_o(x)$ are written into the image memory 150, whereby the abovementioned attenuation information is displayed together with the image 2850 on the display unit 160. Thus, attenuation information for any region of the object under examination can be obtained.

In the foregoing embodiment, it is described that the probe 1 incorporates a plurality of internally located transducers. The probe 1 is, therefore, of the so-called linear array type. Alternatively, however, the probe can be replaced by a single transducer which, while transmitting ultrasonic waves, is scanned at right angles to the direction of transmission, with the transducer receiving echos of the transmitted waves to provide echo signals.

In practicing the present invention, echo intensities of plural frequencies are required. This makes it necessary to use a probe having good sensitivity and response with respect to the frequencies adopted. To realize a probe of this kind, the probe 1 is supplied with a sharply attenuating wide-band drive pulse having a waveform of the type shown at 2210. Preferably, the probe 1 is a transducer made of polymer material (polyvinyldifluoride, or PVDF), a composite transducer made of polymer and inorganic materials, or a PZT transducer provided with an acoustic matching layer, these transducers being designed to have a wide-band characteristic. With a transducer of this type, the ultrasonic pulses transmitted into the interior of the object 1000 from the probe 1 will exhibit a wide band and have a waveform of the kind shown at 2210 in FIG. 1. It is also permissible, as set forth in the specification of Japanese Patent Application No. 55-49571 (Japanese Patent Application Laid-open No. 56-147082) mentioned above, to replace the wide-band probe with a probe that exhibits a plurality of diffferent frequency bands.

Furthermore, in a case where echo intensities having a plurality of frequencies are obtained, as described above, it is permissible to transmit and measure individual ultrasonic signals of a plurality of different frequencies. It is also possible to transmit an ultrasonic signal that contains a plurality of different frequency components. In any case, the expression "ultrasonic waves having a plurality of frequencies" and expressions similar thereto used in the present specification are to be interpreted in their widest sense so as to cover not only individual ultrasonic waves but also an ultrasonic wave made up of a plurality of frequency components.

CONCRETE EFFECT OF THE INVENTION

Thus, according to the present invention, the intensity of an echo obtained from an object under examination as the result of an ultrasonic transmission having a plurality of different frequencies is measured by the so-called synthetic aperture method, whereby the attenuation coefficient of the object and the frequency dependence of the attenuation coefficient can be measured with a minimal error caused by diffusion loss ascribable to diffraction of the transmitted ultrasonic waves. Accordingly, whereas the conventional ultrasonic measurement method and apparatus are capable of providing solely morphological information, the present invention makes it possible to acquire quantitative information relating to attenuation internally of the object under examination.

As many apparently widely different embodiments of the present invention can be made without departing from the spirit and scope thereof, it is to be understood that the invention is not limited to the specific embodiments thereof except as defined in the appended claims.

What we claim is:

1. An ultrasonic measurement method, comprising steps of:
   sequentially scanning ultrasonic transceiving means, which is adapted to transmit generally spherical ultrasonic waves having at least three frequency components toward an object under examination, substantially at right angles to a direction in which the ultrasonic waves are transmitted, during which time said transceiving means receives an echo from the object;
   measuring the intensity of a reflected wave based on said echo and performing a calculation using a synthetic aperture method to obtain a B-scan distribution image of said intensity in the object; and
   calculating an attenuation coefficient of the object based on the intensity of the reflected wave for a scanning position of said transceiving means generally on an extension of a line connecting plural positions of interest designated in the obtained B-scan distribution image.

2. The method according to claim 1, wherein said step for caluculating an attenuation coefficient further comprises the step:
   excluding diffusion loss, incidental to propagation of the transmitted ultrasonic waves, from the calculation of an attenuation coefficient by presuming a sound pressure of the transmitted ultrasonic waves as being solely inversely proportional to the square of a propagation distance due to the diffusion loss.

3. The method according to claim 1, wherein said step for calculating an attenuation coefficient further comprises steps of:
   determining whether there is an additional position of interest which is located at the same distance from said scanning position as either of said plural positions in the obtained B-scan distribution image,
   specifying said additional position of interest and another scanning position of said transceiving means on an extension of a line connecting said additional position of interest and either of the plural positions, only when the exisitence of an additional position of interest has been determined.

4. An ultrasonic measurement apparatus comprising:
   transceiving means having an ultrasonic transducer for transmitting generally spherical ultrasonic waves having at least three frequency components toward an object under examination, and for receiving an echo signal from the object, and scanning means for sequentially scanning said ultrasonic transducer substantially at right angles to a direction in which the ultrasonic waves are transmitted;
   first arithmetic means for measuring the intensity of a reflected wave based on the echo signal from said transceiving means and for performing a calculation based on a synthetic aperture method to obtain a B-scan distribution image of said intensity in the object;
   designating means for designating plural positions of interest in the B-scan distribution image obtained, and
   second arithmetic means for obtaining an attenuation coefficient of the object based on the intensity of the reflected wave for a scanning position of the ultrasonic transducer generally on an extension of a line connecting the plural positions of interest designated.

5. The apparatus according to claim 4, wherein said second arithmetic means calculates a sound pressure of the transmitted ultrasonic waves as being solely inversely proportional to the square of a propagation distance due to the diffusion loss, so that diffusion loss, incidental to propagation of the transmitted ultrasonic waves, from the calculation of an attenuation coefficient may be excluded.

6. The apparatus according to claim 4, further comprising of:
   determination means for determining whether there is an additional position of interest which is located at the same distance from said scanning position as either of said plural positions in the obtained B-scan distribution image, and
   specifying means for specifying said additional position of interest and another scanning position of said transceiving means on an extension of a line connecting said additional position of interest and either of the plural positions, only when the exisitence of an additional position of interest has been determined,
   so that the second arithmetic means calculates an attenuation coefficient based on the intensity of the transmitted ultrasonic waves for the other scanning position.

7. The apparatus according to claim 4, wherein said designating means has display means for visually displaying the B-scan distribution image, with the positions of interest being designated based on the B-scan distribution image displayed on said display means, and said second arithmetic means is further adapted to display the obtained attenuation coefficient on said display means.

* * * * *